(12) United States Patent
Busch et al.

(10) Patent No.: US 6,245,765 B1
(45) Date of Patent: Jun. 12, 2001

(54) MESYLATE DIHYDRATE SALTS OF 5-(2-(4-(1,2-BENZISOTHIAZOL-3-YL)-1-PIPERAZINYL)-ETHYL)-6-CHLORO-1,3-DIHYDRO-2(1H)-INDOL-2-ONE (=ZIPRASIDONE), ITS PREPARATION AND ITS USE AS DOPAMINE D2 ANTAGONIST

(75) Inventors: Frank R. Busch, Gales Ferry; Carol A. Rose, Ledyard; Russell J. Shine, Waterford, all of CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/180,455

(22) PCT Filed: Apr. 10, 1997

(86) PCT No.: PCT/IB97/00393

§ 371 Date: Aug. 30, 1999

§ 102(e) Date: Aug. 30, 1999

(87) PCT Pub. No.: WO97/42191

PCT Pub. Date: Nov. 13, 1997

Related U.S. Application Data

(60) Provisional application No. 60/016,757, filed on May 7, 1996.

(51) Int. Cl.[7] .................... A61K 31/495; A61K 31/50; C07D 209/04; C07D 275/04; C07D 417/00

(52) U.S. Cl. .................... 514/252.13; 514/254.04; 514/254.09; 544/368; 544/376; 544/358; 548/469; 548/503; 548/212; 548/214

(58) Field of Search ........................... 544/376, 358, 544/368; 514/254.04, 254.09, 252.13; 548/469, 503, 212, 214

(56) References Cited

U.S. PATENT DOCUMENTS 5,312,925  5/1994  Allen et al. .

FOREIGN PATENT DOCUMENTS

| | | |
|---|---|---|
| 0281309 A1 | 9/1988 | (EP) . |
| 0584903 A1 | 3/1994 | (EP) . |
| 0586191 A1 | 3/1994 | (EP) . |
| 9500510 | 1/1995 | (WO) . |
| 9742190 | 11/1997 | (WO) . |

OTHER PUBLICATIONS

Howard H. R., et al., (1996) 3–Benzisothiazolylpiperazine Derivatives as Potential Atypical Antipsychotic Agents, Journal of Medicinal Chemistry, vol. 39, pp. 143–148.

*Primary Examiner*—Mukund J. Shah
*Assistant Examiner*—Sudhaker B. Patel
(74) *Attorney, Agent, or Firm*—Peter C. Richardson; Paul H. Ginsburg; Kristina L. Konstas

(57) ABSTRACT

The invention is directed to the mesylate dihydrate salts of 5-(2-(4-(1,2-benzisothiazol-3-yl)-1-piperazinyl)ethyl)-6-chloro-1,3-dihydro-2H-indol-2-one, pharmaceutical compositions containing said ziprasidone mesylate dihydrates, and methods of adminsitering the ziprasidone mesylate dihydrates to treat psychotic diseases.

9 Claims, 6 Drawing Sheets

1 cm = 110 µm 1 cm = 55 μm 1 cm = 55 μm

MESYLATE DIHYDRATE SALTS OF 5-(2-(4-(1,2-BENZISOTHIAZOL-3-YL)-1-PIPERAZINYL)-ETHYL)-6-CHLORO-1,3-DIHYDRO-2(1H)-INDOL-2-ONE (=ZIPRASIDONE), ITS PREPARATION AND ITS USE AS DOPAMINE D2 ANTAGONIST

This application is a 371 of PCT/IB97/00393 filed Apr. 10, 1997, and also claim benefit of Provisional No. 60/016,757 filed May 7, 1996.

BACKGROUND OF THE INVENTION

The invention is directed to the mesylate dihydrate salts of 5-(2-(4-(1,2-benzisothiazol-3-yl)-1-piperazinyl)ethyl)-6chloro-1,3-dihydro-2H-indol-2-one (hereafter "ziprasidone mesylate dihydrates"), pharmaceutical compositions containing one or both of the ziprasidone mesylate dihydrates, and methods of administering the ziprasidone mesylate dihydrates to treat psychotic diseases. Ziprasidone is a potent antipsychotic agent and is therefore useful for treating various disorders including schizophrenia, anxiety and migraine pain. U.S. Pat. No. 5,312,925 refers to ziprasidone hydrochloride monohydrate, and states that ziprasidone hydrochloride monohydrate is substantially hygroscopically stable, which alleviates potential problems associated with weight changes of the active ingredient during the manufacture of capsules or tablets. U.S. Pat. No. 5,312,925 is herein incorporated by reference in its entirety. Ziprasidone hydrochloride monohydrate, however, has low aqueous solubility and, as a result, is more appropriate for capsule or tablet formulation than for injectable dosage forms.

The ziprasidone mesylate dihydrates also possess hygroscopic stability. The ziprasidone mesylate dihydrates have the added advantage of having significantly greater aqueous solubility than the hydrochloride monohydrate, which makes the mesylate dihydrates more suitable for injectable dosage forms than the hydrochloride monohydrate.

SUMMARY OF THE INVENTION

The present invention relates to the mesylate dihydrate salts of 5-(2-(4-(1,2-benzisothiazol-3-yl)-1-piperazinyl)ethyl)-chloro-1,3-dihydro-2H-indol-2-one.

This invention also relates to a pharmaceutical composition for the treatment of a psychotic disorder, such as schizophrenia, anxiety or migraine pain, comprising an amount of the mesylate dihydrate salts of 5-(2-(4-(1,2-benzisothiazol-3yl)-1-piperazinyl)ethyl)-6-chloro-1,3-dihydro-2H-indol-2-one that is effective in treating said psychotic disorder, and a pharmaceutically acceptable carrier.

This invention also relates to a method of treating a psychotic disorder, such as schizophrenia, anxiety or migraine pain, in a mammal, including a human, comprising administering to said mammal an amount of the mesylate dihydrate salts of 5-(2-(4-(1,2-benzisothiazol- 3-yl)-1-piperazinyl)ethyl)chloro-1,3-dihydro-2H-indol-2-one that is effective in treating said disorder.

Figure 1:
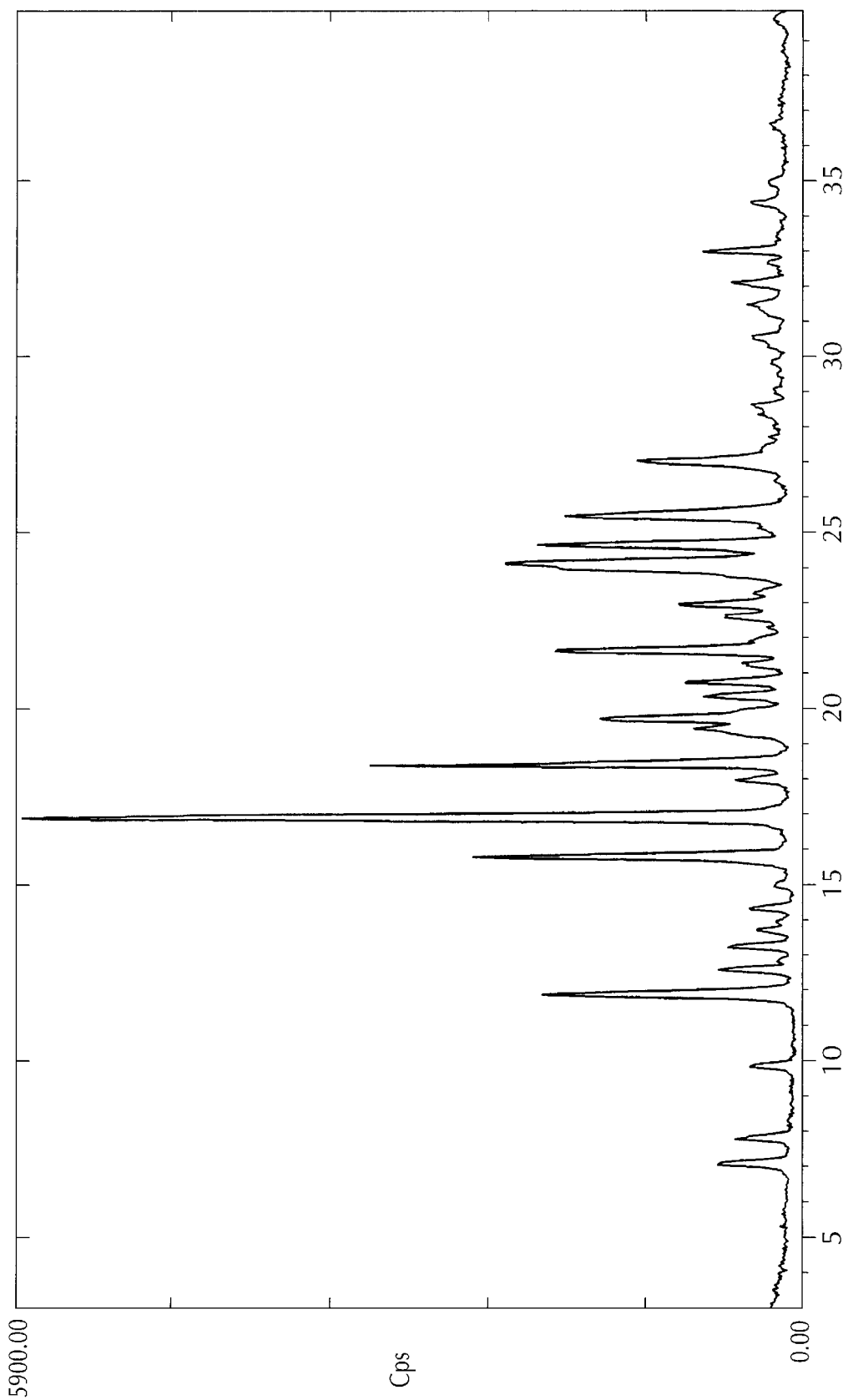
FIG. 1 depicts the X-ray powder diffraction spectrum of ziprasidone mesylate dihydrate (lath crystal) expressed as intensity (Cps) versus diffraction angle (two-theta degrees).

Tables 1–3 below identify selected peaks from the spectra of FIGS. 1–3, respectively, by diffraction angle (two-theta), d-spacing, maximum intensity (max, int.), and relative intensity (rel. int.).

TABLE 1

X-RAY POWDER DIFFRACTION DATA FOR ZIPRASIDONE MESYLATE DIHYDRATE (LATH CRYSTALS)

| Two-Theta (degrees) | D-spacing (degrees) | Max. Int. (counts/sec) | Rel. Int. (%) |
|---|---|---|---|
| 3.080 | 28.6618 | 245.00 | 4.19 |
| 3.684 | 23.9618 | 210.00 | 3.60 |
| 7.208 | 12.2538 | 626.00 | 10.71 |
| 7.931 | 11.1377 | 493.00 | 8.44 |
| 8.429 | 10.4810 | 100.00 | 1.71 |
| 9.968 | 8.8664 | 386.00 | 6.61 |
| 12.022 | 7.3558 | 1947.00 | 33.33 |
| 12.721 | 6.9527 | 620.00 | 10.61 |
| 13.394 | 6.6049 | 548.00 | 9.38 |
| 13.886 | 6.3720 | 331.00 | 5.67 |
| 14.481 | 6.1116 | 390.00 | 6.68 |
| 15.152 | 5.8426 | 194.00 | 3.32 |
| 15.949 | 5.5523 | 2462.00 | 42.15 |
| 17.048 | 5.1967 | 5841.00 | 100.00 |
| 18.111 | 4.8941 | 493.00 | 8.44 |
| 18.592 | 4.7684 | 3227.00 | 55.25 |
| 19.520 | 4.5438 | 740.00 | 12.67 |
| 19.862 | 4.4663 | 1512.00 | 25.89 |
| 20.517 | 4.3253 | 733.00 | 12.55 |
| 20.883 | 4.2503 | 872.00 | 14.93 |
| 21.372 | 4.1541 | 412.00 | 7.05 |
| 21.814 | 4.0709 | 1848.00 | 31.64 |
| 22.711 | 3.9121 | 571.00 | 9.78 |
| 23.078 | 3.8507 | 920.00 | 15.75 |
| 24.263 | 2.6652 | 2218.00 | 37.97 |
| 24.798 | 3.5874 | 1982.00 | 33.93 |
| 25.665 | 3.4681 | 1778.00 | 30.44 |
| 26.640 | 3.3434 | 204.00 | 3.49 |
| 27.162 | 3.2803 | 1232.00 | 21.09 |
| 28.728 | 3.1049 | 347.00 | 5.94 |
| 29.202 | 3.0556 | 209.00 | 3.58 |
| 30.004 | 2.9758 | 225.00 | 3.85 |
| 30.721 | 2.9079 | 366.00 | 6.27 |
| 31.610 | 2.8281 | 407.00 | 6.97 |
| 32.267 | 2.7720 | 522.00 | 8.94 |
| 32.800 | 2.7282 | 252.00 | 4.31 |
| 33.202 | 2.6960 | 743.00 | 12.72 |
| 34.549 | 2.5940 | 373.00 | 6.39 |
| 34.549 | 2.5940 | 373.00 | 6.39 |
| 35.144 | 2.5514 | 245.00 | 4.19 |
| 36.738 | 2.4443 | 220.00 | 3.77 |
| 38.910 | 2.3127 | 124.00 | 2.12 |
| 39.751 | 2.2657 | 204.00 | 3.49 |

TABLE 2

X-RAY POWDER DIFFRACTION DATA FOR
ZIPRASIDONE MESYLATE DIHYDRATE
(NEEDLE CRYSTALS)

| Two-Theta (degrees) | D-spacing (degrees) | Max. Int. (counts/sec) | Rel. Int. (%) |
|---|---|---|---|
| 7.823 | 11.2913 | 33.00 | 1.78 |
| 10.049 | 8.7946 | 504.00 | 27.20 |
| 11.502 | 7.6872 | 1095.00 | 59.09 |
| 12.660 | 6.9866 | 148.00 | 7.99 |
| 13.440 | 6.5826 | 87.00 | 4.70 |
| 14.080 | 6.2848 | 83.00 | 4.48 |
| 14.958 | 5.9178 | 791.00 | 42.69 |
| 15.762 | 5.6179 | 446.00 | 24.07 |
| 16.313 | 5.4293 | 398.00 | 21.48 |
| 16.760 | 5.2854 | 140.00 | 7.56 |
| 17.261 | 5.1330 | 71.00 | 3.83 |
| 17.696 | 5.0078 | 125.00 | 6.75 |
| 18.640 | 4.7563 | 631.00 | 3405 |
| 19.002 | 4.6665 | 1853.00 | 100.00 |
| 19.976 | 4.4411 | 294.00 | 15.87 |
| 20.726 | 4.2820 | 115.00 | 6.21 |
| 22.348 | 3.9748 | 470.00 | 25.36 |
| 22.790 | 3.8987 | 1440.00 | 77.71 |
| 24.377 | 3.6484 | 884.00 | 47.71 |
| 25.368 | 3.5080 | 192.00 | 10.36 |
| 25.861 | 3.4423 | 457.00 | 24.66 |
| 26.640 | 3.3434 | 150.00 | 8.09 |
| 27.172 | 3.2743 | 329.00 | 17.75 |
| 28.349 | 3.1456 | 309.00 | 16.68 |
| 28.930 | 3.0837 | 180.00 | 9.71 |
| 29.644 | 3.0111 | 231.00 | 12.47 |
| 30.130 | 2.9636 | 175.00 | 9.44 |
| 30.601 | 2.9190 | 236.00 | 12.74 |
| 31.704 | 2.8200 | 95.00 | 5.13 |
| 32.198 | 2.7778 | 83.00 | 4.48 |
| 33.887 | 2.6431 | 98.00 | 5.29 |
| 34.830 | 2.5737 | 124.00 | 6.69 |
| 35.519 | 2.5253 | 106.00 | 5.72 |
| 36.901 | 2.4339 | 63.00 | 3.40 |
| 37.716 | 2.3831 | 110.00 | 5.94 |
| 38.331 | 2.3463 | 113.00 | 6.10 |
| 38.732 | 2.3229 | 146.00 | 7.88 |
| 39.751 | 2.2657 | 105.00 | 5.67 |

TABLE 3

X-RAY POWDER DIFFRACTION DATA FOR
ZIPRASIDONE MESYLATE ANHYDROUS (LATH CRYSTALS)

| Two-Theta (degrees) | D-spacing (degrees) | Max. Int. (counts/sec) | Rel. Int. (%) |
|---|---|---|---|
| 3.065 | 28.8018 | 120.00 | 9.16 |
| 6.521 | 13.5424 | 63.00 | 4.81 |
| 8.737 | 10.1124 | 72.00 | 5.50 |
| 11.860 | 7.4557 | 38.00 | 2.90 |
| 12.776 | 6.9231 | 528.00 | 40.31 |
| 13.992 | 6.3241 | 386.00 | 29.47 |
| 16.307 | 5.4311 | 653.00 | 49.85 |
| 16.847 | 5.2582 | 448.00 | 34.20 |
| 17.538 | 5.0527 | 608.00 | 46.41 |
| 18.385 | 4.8217 | 369.00 | 28.17 |
| 18.800 | 4.7162 | 169.00 | 12.90 |
| 19.712 | 4.5001 | 1310.00 | 100.00 |
| 20.722 | 4.2829 | 208.00 | 15.88 |
| 21.424 | 4.1441 | 932.00 | 71.15 |
| 22.600 | 3.9311 | 509.00 | 38.85 |
| 22.918 | 3.8772 | 658.00 | 50.23 |
| 23.690 | 3.7526 | 502.00 | 38.32 |
| 24.558 | 3.6219 | 743.00 | 56.72 |
| 25.792 | 3.4513 | 175.00 | 13.36 |
| 26.399 | 3.3734 | 612.00 | 46.72 |
| 28.185 | 3.1636 | 109.00 | 8.32 |
| 28.706 | 3.1073 | 82.00 | 6.26 |
| 29.652 | 3.0103 | 135.00 | 10.31 |
| 30.680 | 2.9117 | 104.00 | 7.94 |
| 31.034 | 2.8793 | 171.00 | 13.05 |
| 31.365 | 2.8497 | 152.00 | 11.60 |
| 32.983 | 2.7135 | 98.00 | 7.48 |
| 33.737 | 2.6545 | 101.00 | 7.71 |
| 35.533 | 2.5244 | 63.00 | 4.81 |
| 38.737 | 2.3226 | 92.00 | 7.02 |
| 39.608 | 2.2735 | 73.00 | 5.57 |

DETAILED DESCRIPTION OF THE INVENTION

Figure 4:
FIG. 4 shows a photomicrograph of ziprasidone mesylate dihydrate (lath crystals).
Figure 5:
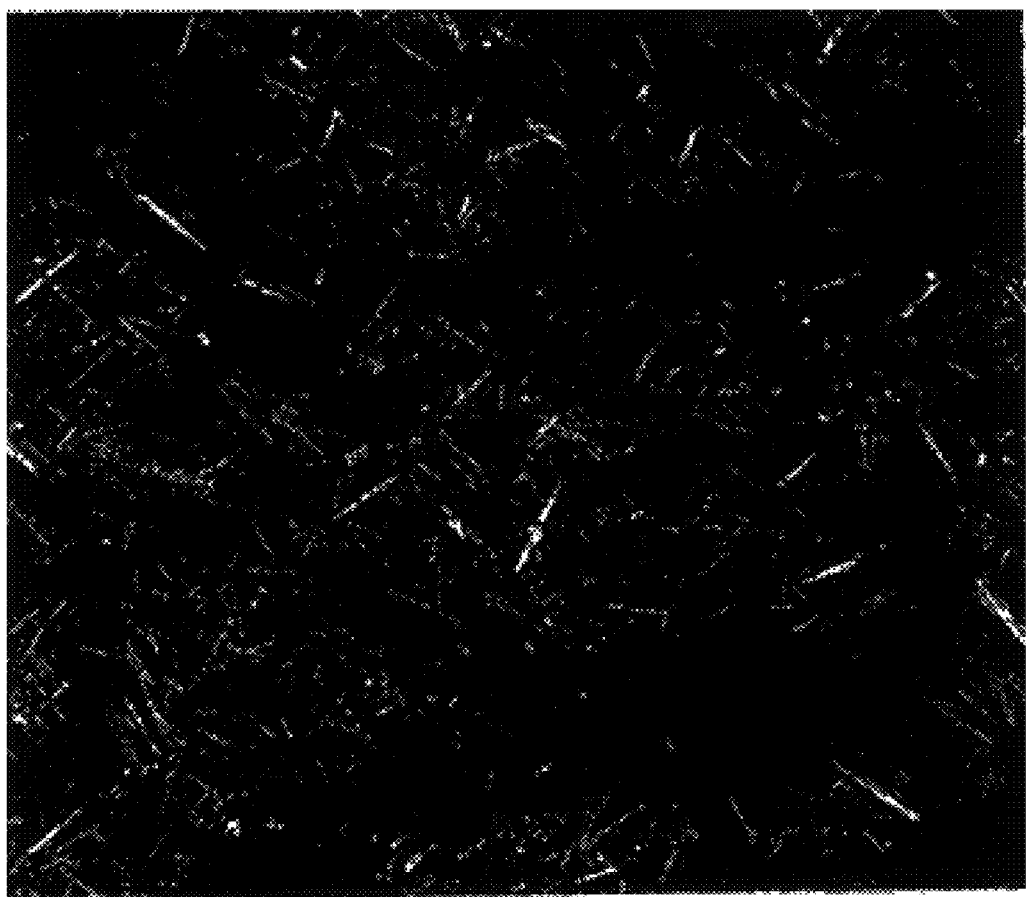
FIG. 5 shows a photomicrograph of ziprasidone mesylate dihydrate (needle crystals).
Figure 6:
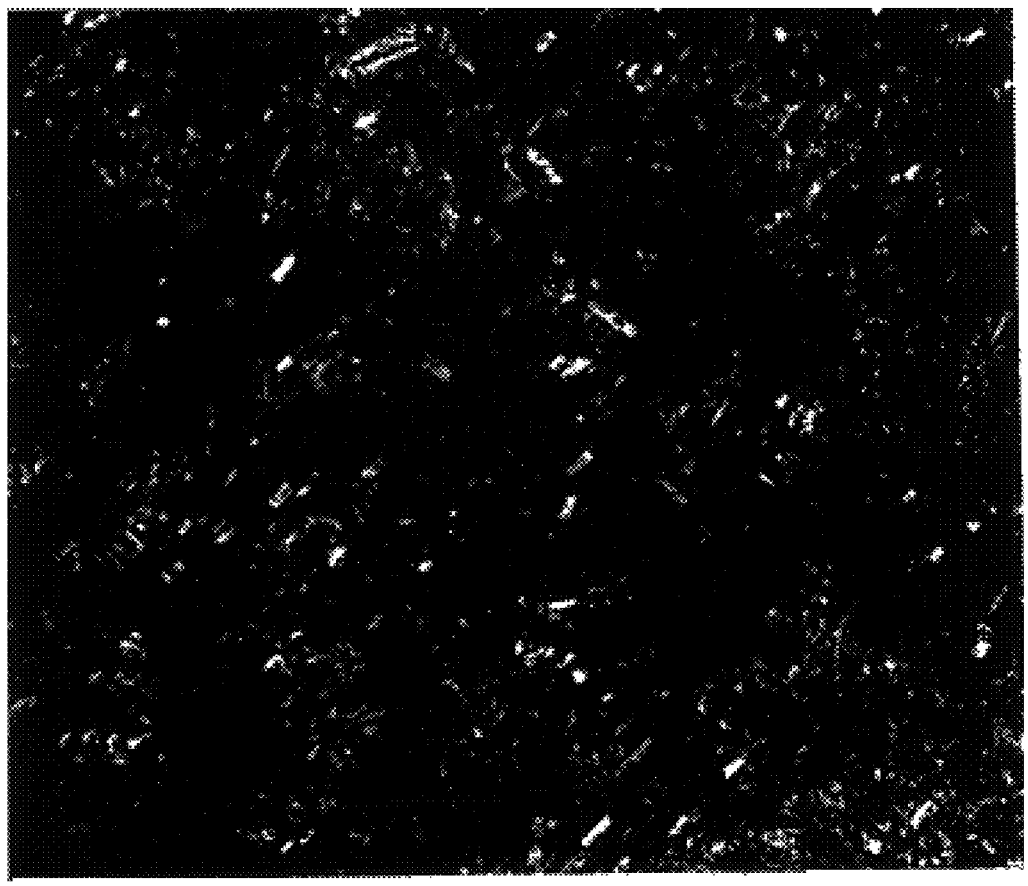
FIG. 6 shows a photomicrograph of ziprasidone mesylate anhydrous (lath crystals).

Ziprasidone mesylate exists in four distinct crystalline forms: ziprasidone mesylate anhydrous (lath crystal), ziprasidone mesylate dihydrate (lath crystal), ziprasidone mesylate dihydrate (needle crystal), and ziprasidone mesylate trihydrate. Each crystal form has distinct characteristics, such as a distinct powder X-ray diffraction pattern and a distinct crystal shape that can be observed by photomicrograph. The ziprasidone mesylate dihydrate lath (FIG. 4) and needle (FIG. 5) crystals are relatively long and thin in contrast to the prism crystals of ziprasidone mesylate trihydrate. Ziprasidone mesylate anhydrous crystals (FIG. 6) are distinct, though similar in shape to the dihydrate lath crystals. The photomicrographs of FIGS. 4–6 were obtained using an Olympus polarizing microscope (model BH-2) equiped with a halogen lamp, binocular eye piece, polarizing filter and Sony 3ccd video camera with Sony color printer.

Figure 2:
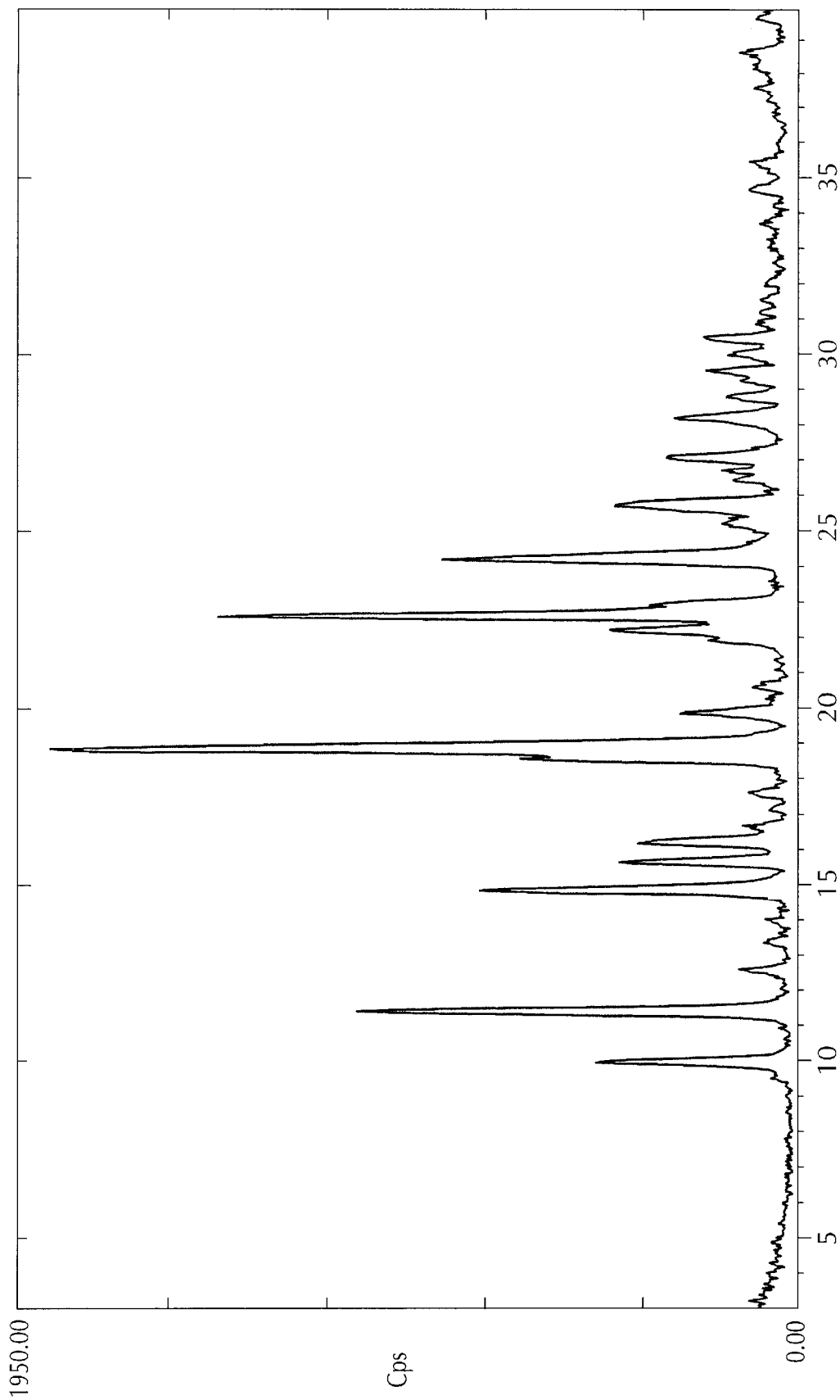
FIG. 2 depicts the X-ray powder diffraction spectrum of ziprasidone mesylate dihydrate (needle crystal) expressed as intensity (Cps) versus diffraction angle (two-theta degrees).
Figure 3:
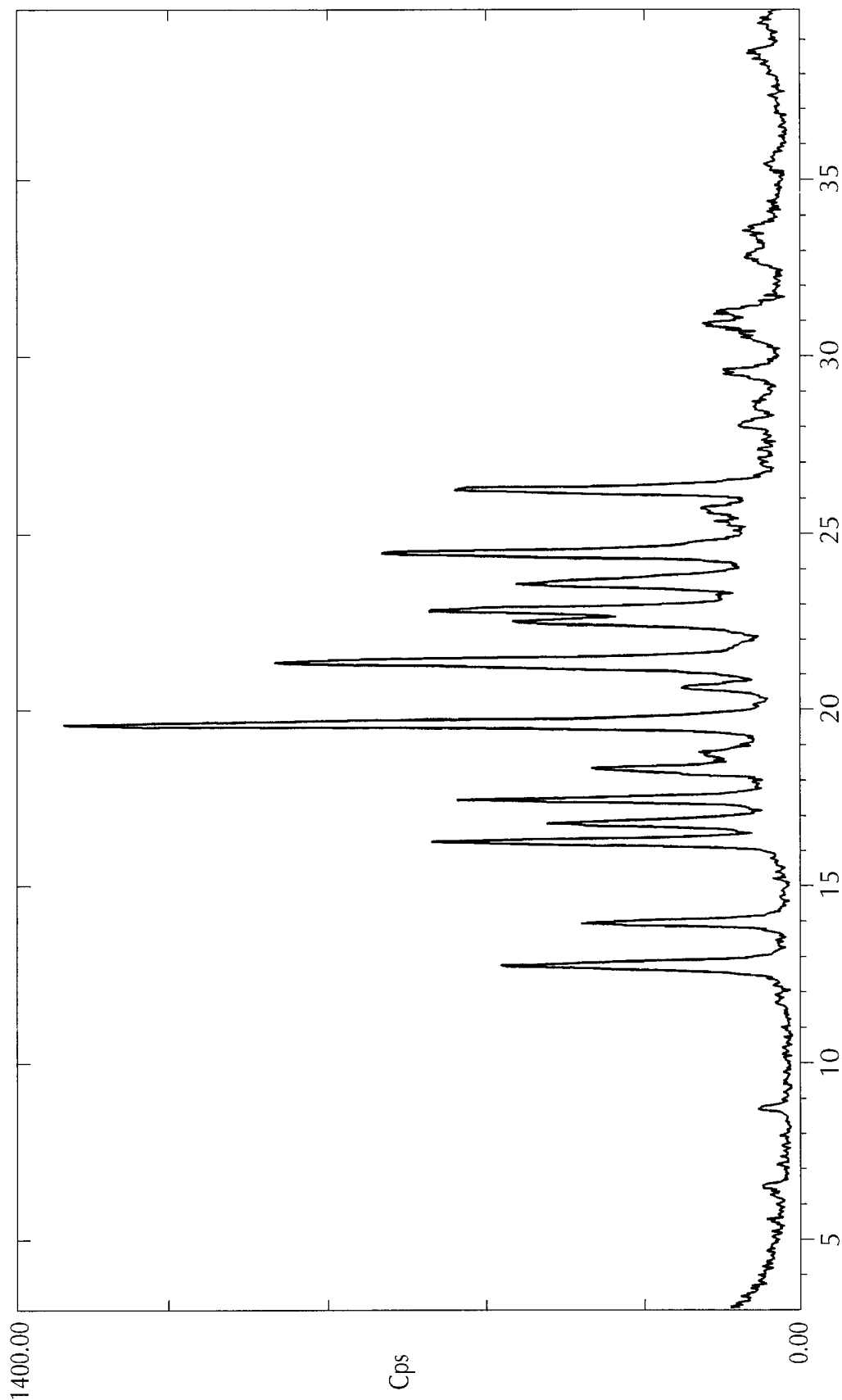
FIG. 3 depicts the X-ray powder diffraction spectrum of ziprasidone mesylate anhydrous (lath crystal) expressed as intensity (Cps) versus diffraction angle (two-theta degrees).

The characteristic X-ray powder diffraction spectra of the ziprasidone mesylate dihydrates are depicted in FIGS. 1 and 2. While the ziprasidone mesylate anhydrous crystals (FIG. 6) may be similar to the dihydrate lath crystals (FIG. 4) in shape, the X-ray powder diffraction spectrum of ziprasidone mesylate anhydrous (FIG. 3) is clearly distinct from the X-ray powder diffraction spectra of the ziprasidone mesylate dihydrates (FIGS. 1 and 2). The X-ray powder diffraction spectra of FIGS. 1–3 were taken on a Siemens R3RA/v diffractometer. The ziprasidone mesylate dihydrates are further characterized by their water content which is indicated by their Karl Fischer (KF) value of 6.4±1.0. Ziprasidone mesylate trihydrate is the subject of co-pending United States provisional application Ser. No. 60/016,537 entitled "Mesylate Trihydrate of 5-(2-(4-(1,2-Benzisothiazol-3-yl)-1-piperazinyl)ethyl)-6-chloro-1,3-dihydro-2H-indol-2-one" (Pfizer docket number PC9277), filed concurrently herewith. The foregoing co-pending United States provisional application is incorporated herein by reference in its entirety.

The ziprasidone mesylate dihydrates are significantly more soluble in an aqueous medium than ziprasidone hydrochloride monohydrate which has a solubility of 0.08 mg/ml in water at ambient temperature. The aqueous solubility of the four ziprasidone mesylate forms is indicated in Table 4 below.

TABLE 4

Aqueous Solubility Of Ziprasidone Mesylate Polymorphs

| POLYMORPH | SOLUBILITY IN WATER |
|---|---|
| trihydrate | 0.73 mg/mL |
| dihydrate (lath) | 1.11 mg/mL |
| dihydrate (needle) | 1.10 mg/mL |
| anhydrous | 1.27 mg/mL |

The ziprasidone mesylate dihydrates may be prepared from the free base (ziprasidone) which is prepared as described in column 4, lines 22–43 of U.S. Pat. No. 5,312,925, referred to above. The tree base can also be prepared as described in U.S. Pat. No. 5,338,846, the disclosure of which is herein incorporated by reference in its entirety. When the intended use is as an injectable formulation, it is preferred to conduct the preparation under pyrogen-free and speck-free conditions. Speck-free solvents and reagents can be prepared by filtering them through a 0.45 μm Millipore® nylon filter.

Ziprasidone mesylate dihydrate needle crystals are prepared by mixing the free base with a mixture of water and organic solvent, adding dilute methanesulfonic acid, and heating to reflux as described above for the preparation of the trihydrate. The dihydrate needle crystals are prepared by adding a seed crystal of the needle shaped polymorph to the reaction solution after the solution has been stirred under reflux conditons for about thirty minutes. A thick "pinkish" slurry indicating crystal formation will begin to form. The reaction solution is then allowed to cool slowly with stirring. During cooling at about 50° C., water can be added to the solution to thin the slurry. The needle crystals can be filtered from the composition through a poly-cloth filter, and then washed consecutively with appropriate volumes of a THF/water (65/35, v/v) solution and water. When allowed to dry at ambient temperature, the water content of the needle crystals has a Karl Fischer value ranging from 6.0–6.8% KF (theoretical KF for the trihydrate is 6.4 %).

Ziprasidone dihydrate lath crystals are prepared by mixing the free base with water and warming the resulting slurry to 50° C. to 55° C. Concentrated methanesulfonic acid is then added and the mixture is heated to reflux. After about 1 to 6 hours, preferably 2 hours, at reflux, the solution is cooled to provide the dihydrate lath crystals. The resulting slurry is stirred for about 2 hours at ambient temperature and the crystals are then filtered from the composition and washed as described above for the needle crystals. When allowed to dry at ambient temperature, the water content of the lath crystals has a Karl Fischer value ranging from 6.0% to 6.8 % (theoretical KF for the dihydrate is 6.4%).

The ziprasidone mesylate dihydrates may be administered as a psychotic agent as described in U.S. Pat. No. 5,312,925, referred to above. Administration of ziprasidone mesylate dihydrate is preferably done in combination with pharmaceutically acceptable carriers or diluents in a pharmaceutical composition, in accordance with standard pharmaceutical practice and as described in U.S. Pat. No. 5,312,925, referred to above. Suitable pharmaceutical carriers include solid diluents or fillers, and sterile aqueous solutions, various organic solvents and excipients known to those skilled in the art.

The ziprasidone mesylate dihydrates may be administered orally or parenterally, including intravenously or intramuscularly. For parenteral administration, it is preferred, where the use of water is called for, to use sterile water for injection (SWI). Administration through intramuscular injection is preferred. A preferred composition for intramuscular injection is ziprasidone mesylate dihydrate (needle or lath, or both) in combination with sulfoxybutyl β-cyclodextrin as carrier, preferably prepared at a ratio of 1:10 (w/w) dihydrate to carrier. Compositions containing ziprasidone mesylate dihydrate (needle or lath) in combination with sulfoxy β-cyclodextrin can be prepared as described in co-pending United States provisional applications Ser. No. 60/016,866 entitled "Method Of Making Inclusion Complexes" (Pfizer docket number PC 9563), filed concurrently herewith, and Ser. No. 60/019,204 "Inclusion Complexes Of Aryl-Heterocyclic Compounds" (Pfizer docket number PC 8838), filed concurrently herewith. Both of the foregoing co-pending United States provisional applications are incorporated herein by reference in their entirety.

The effective dosage for the ziprasidone mesylate dihydrates depends on the intended route of administration, the indication to be treated, and other factors such as age and weight of the subject. In the following dosage ranges, the term "mgA" refers milligrams of the free base (ziprasidone). A recommended range for oral dosing is 5–300 mgA/day, preferably 40–200 mgA/day, more preferably 40–80 mgA/day, in single or divided doses. A recommended range for parenteral adiministration, such as injection, is 2.5 mgA/day to 160 mgA/day, and preferably 5–80 mgA/day.

The present invention is illustrated by the following examples, but it is not limited to the details thereof. Unless otherwise indicated, the preparations described in the following examples were conducted under speck-free and pyrogen-free conditions. As used in the following examples, THF means tetrahydrofuran and SWI means sterile water for injection.

EXAMPLE 1

Purification of 5-[2-[4-(1,2-benzisothzol-3-yl)-1-piperazinyl]ethyl]-6-chloro-1,3-dihydro-2H-indol-2-one To a clean and dry glass-lined tank, 46.8 kg of 5-[2-[4-(1,2-benzisothiazol-3-yl)-1-piperazinyl]ethyl]-6-chloro-1,3-dihydro-2H-indol-2-one and 2816.4 L of THF were charged. The slurry was heated to reflux and held for forty-five minutes to form a hazy solution. The solution was filtered through a 33-inch sparkler precoated with filter aid and backed with a Fulflo® filter (manufactured by Parker Hanndin Corp., Lebanon, Ind.) to a clean, dry glass-lined tank on a lower level. The filtered solution was concentrated by vacuum distillation, cooled to 5° C., and allowed to stir for two hours. The product was collected by filtration on a centrifuge and washed with cold (0–50° C.) THF. The product was collected and dried under vacuum at 45° C., to yield 40.5 kg of product. The product had a purity of 101.5% (within the typical range of 100±2% vs. the standard) as determined by an HPLC assay.

EXAMPLE 2

5-[2-[4-(1-benzisothiazol-3-yl)-1-piperazinyl]ethyl]-6-chloro-1,3-dihydro-2H-indol-2-one methanesulfonate trihydrate A slurry was produced by charging 1000 g of 5-[2-[4-(1,2-benzisothiazol-3-yl)-1-piperazinyl]ethyl]-6-chloro-1,3dihydro-2H-indol-2-one, 7500 mL of SWI, and 4000 mL of THF to a 22-liter, three-neck, round-bottom flask equipped with a heating mantle, an overhead mechanical stirrer, a condenser, and a temperature probe. The flask contents were protected from light with an aluminum foil cover. The slurry was heated to 50° C. while stirring. Dilute methanesulfonic acid was prepared by combining 188 mL of methanesulfonic acid with 812 mL SWI. The dilute methanesulfonic acid was added slowly through a dropping funnel to the reaction mixture. The reaction was heated to reflux (about 65° C.), and a dark red solution formed as the reaction mixture was heated. The reaction mixture was allowed to stir under reflux conditions for approximately thirty minutes. After the thirty minute time period, the heating mantle was shut off to allow slow cooling of the reaction mixture with stirring. The reaction mixture was allowed to cool with stirring overnight (about 18 hours). As the reaction mixture cooled, the product crystallized out as large "yellowish" hexagonal prismatic crystals. The mixture was allowed to stir under ambient conditions for one hour. The product was isolated on a Buchner funnel with a poly cloth filter and was washed consecutively with 1500 mL of THF/SWI (65/35, v/v) and 1000 mL of SWI. The crystals were spread over glass trays and allowed to dry under ambient conditions to a Karl Fischer value of about 9.6%. The product was milled through a Mikro-Sampimill® (manufactured by the Pulverizing Machinery Division of Mikropul Corp., Summit, N.J.) equipped with a 0.027 H plate at a speed of 14,000 rpm. The yield was 945 g of product.

The product's structure was confirmed as 5-[2-[4-(1,2-benzisothiazol-3-yl)-1-piperazinyl]ethyl]-6-chloro-1,3-dihydro-2H-indol-2-one methanesulfonate trihydrate by NMR. $^{13}$C NMR (DMSO-d$_6$): δ 177.1(0), 163.0(0), 153.0 (0), 145.0(0), 132.4(0), 129.0(1), 127.8(0), 127.7(1), 127.1 (0), 126.5(0), 125.6(1), 124.9 91), 122.1(1), 110.6(1), 55.9 (2), 51.7(2), 47.5(2), 40.7(3), 36.2(2), 27.9(2). $^1$H NMR (DMSO-d$_6$): δ 10.5 (s, 11H); 9.8 (br. s, 1H); 8.2 (d, J=8.2 Hz, 1H); 8.1 (d, J=8.2 Hz, 1H); 7.6 (m, 1H), 7.5 (m, 1H); 7.3 (s, 1H), 6.9 (s, 1H); 4.2 (m, 2H); 3.7 (m, 2H); 3.5 (m, 2H), 3.4 (m, 2H); 3.1 (m, 2H); 2.4 (s, 3H).

Evaluation of the product by HPLC showed a peak with a retention time corresponding to that of a standard. The HPLC conditions are summarized in Table 5 below.

TABLE 5

| HPLC Conditions: | |
|---|---|
| Column: | Waters-Puresil C-18 15 cm length × 4.6 mm I.D. (Catalog No. WATO44345) |
| Mobile phase: | 0.05 M KH$_2$PO$_4$ pH 3.0:methanol (60:40 v/v) |
| Flow rate: | 2.0 mL/minute |
| Detection: | UV, 229 nm |
| Column temperature: | ambient |
| Sample volume: | 10 μL |

EXAMPLE 3

5-[2-[4-(1,2-benzisothiazol-3-yl)-1-piperazinyl] ethyl]-6-chloro-1,3-dihydro-2H-indol-2-one methanesulfonate Anhydrous A slurry was produced by charging 350 g of 5-[2-[4-(1, 2-benziosothiazol-3-yl)-1-piperazinyl]ethyl]-chloro-1,3-dihydro-2H-indol-2-one and 7000 mL of isopropanol to a 12-liter three-neck, round-bottom flask equipped with a heating mantle, an overhead mechanical stirrer, a condenser, and a temperature probe. The slurry was heated to 50° C. while stirring. 65.9 mL of methanesulfonic acid was added slowly through a dropping funnel to the 50° C. reaction mixture. A slight exotherm to 55° C. along with thickening of the slurry and lightening of the slurry color were observed. The reaction was atmospherically distilled to remove 25% of the volume (1750 mL). The slurry was cooled to ambient temperature and allowed to stir overnight. The product was isolated on a sintered glass funnel and washed with fresh isopropanol. The solids were spread over glass trays and allowed to dry under ambient conditions to a Karl Fischer value of 0.5%. The yield was 420.3 g of product. Evaluation of the product by HPLC showed a peak with a retention time corresponding to that of a standard. The purity of the product, as determined by HPLC (conditions in Table 5), was 99.8%.

EXAMPLE 4

5-[2-[4-(1,2-benzisothiazol-3-yl)-1-piperazinyl] ethyl]-6-chloro-1,3-dihydro-2H-indol-2-one Methanesulfonate Dihydrate (Needle Crystals)

A slurry was produced by charging 5 g of 5-[2-[4-(1,2-benzisothiazol-3-yl)-1-piperazinyl]ethyl]-6-chloro-1,3-dihydro-2H-indol-2-one, 37.5 mL of water, and 20 mL of THF to a 150 mL, three-neck, round-bottom flask equipped with a heating mantle, an overhead mechanical stirrer, a condenser, and a temperature probe. The flask contents were protected from light with an aluminum foil cover. The slurry was heated to 65° C. with stirring. Dilute methanesulfonic acid was prepared by combining 1 mL of methanesulfonic acid with 4 mL SWI. The dilute methanesulfonic acid was added slowly through a dropping funnel to the reaction mixture. The reaction was heated to reflux (about 65° C.) and a dark red solution formed. The reaction mixture was allowed to stir under reflux conditions for approximately thirty minutes. After the thirty minute period, a seed crystal of the needle shaped polymorph was added to the reaction solution. Crystal formation started, and the heat was removed to allow slow cooling of the reaction with stirring. During cooling at 50° C., a thick "pinkish" slurry was observed in the flask. Water (20 mL) was added to the flask to thin the slurry. The product was allowed to stir under ambient conditions for one hour. The product was isolated on a Buchner funnel with a paper filter and the solids were allowed to dry under ambient conditions to a Karl Fischer value of about 6.6%. The yield was 6.03 g of product. The purity of the product, as determined by HPLC (conditions in Table 5), was 99.8%.

EXAMPLE 5

5-[2-[4-(1,2-benzisothiazol-3-yl)-1-piperazinyl] ethyl]-6-chloro-1,3-dihydro-2H-indol-2one Methanesulfonate Dihydrate (Lath Crystals)

A slurry was produced by charging 25 g of 5-[2-[4-(1,2-benzisothiazol-3-yl)-1-piperazinyl]ethyl]-6-chloro-1,3-dihydro-2H-indol-2-one and 375 mL of water to a 500 mL, three-neck, round-bottom flask equipped with a heating mantle, an overhead mechanical stirrer, a condenser, and a temperature probe. The flask contents were protected from light with an aluminum foil cover. The slurry was heated to 50–55° C. while stirring. Methanesulfonic acid (5 mL) was added slowly through a dropping funnel to the reaction mixture. Thickening of the slurry and lightening of the slurry color were observed. The reaction was heated to reflux (about 100° C.) and allowed to stir for about one hour. The heat was removed to allow slow cooling of the reaction with stirring. The reaction solution was allowed to stir under ambient conditions for about one hour. The product was isolated on a Buchner funnel with a paper filter and the solids were allowed to dry under ambient conditions to a Karl Fischer value of about 6.2%. The yield was 32.11 g of product. The purity of the product, as determined by HPLC (conditions in Table 5), was 98.7%.

We claim:

1. A mesylate dihydrate salt of 5-(2-(4-(1,2-benzisothiazol-3-yl)-1-piperazinyl)ethyl)-6-chloro-1,3dihydro-2H-indol-2-one.

2. The compound of claim 1 in the form of lath crystals.

3. The compound of claim 1 in the form of needle crystals.

4. A pharmaceutical composition for the treatment of a psychotic disorder comprising an amount of the compound of claim 1 that is effective in the treatment of said psychotic disorder and a pharmaceutically acceptable carrier.

5. A method of treating a psychotic disorder in a mammal comprising administering to said mammal an amount of the compound of claim 1 that is effective in the treatment of said psychotic disorder.

6. The method of claim 5 wherein said disorder is schizophrenia, anxiety or migraine pain.

7. The method of claim 5 wherein said disorder is schizophrenia.

8. The method of claim 5 wherein said administration is parenteral administration.

9. The method of claim 8 wherein said parenteral administration is intramuscular injection.

* * * * *